US009222108B2

(12) United States Patent
Gray

(10) Patent No.: US 9,222,108 B2
(45) Date of Patent: Dec. 29, 2015

(54) BIOREACTOR PROCESS FOR PRODUCTION OF HYDROGEN FROM BIOMASS

(75) Inventor: Vincent Myles Gray, Johannesburg (ZA)

(73) Assignee: University of The Witwatersrand, Johannesburg, Johannesburg (ZA)

(*) Notice: Subject to any disclaimer, the term of this patent is extended or adjusted under 35 U.S.C. 154(b) by 885 days.

(21) Appl. No.: 13/320,493

(22) PCT Filed: May 14, 2010

(86) PCT No.: PCT/IB2010/052143
§ 371 (c)(1),
(2), (4) Date: Dec. 6, 2011

(87) PCT Pub. No.: WO2010/131224
PCT Pub. Date: Nov. 18, 2010

(65) Prior Publication Data
US 2012/0088266 A1 Apr. 12, 2012

(30) Foreign Application Priority Data

May 14, 2009 (ZA) .................................. 2009/03330

(51) Int. Cl.
| | |
|---|---|
| C12P 3/00 | (2006.01) |
| C12P 1/04 | (2006.01) |
| C12R 1/01 | (2006.01) |
| C12M 1/107 | (2006.01) |
| C12M 1/12 | (2006.01) |
| C12M 1/00 | (2006.01) |

(52) U.S. Cl.
CPC ... *C12P 3/00* (2013.01); *C12P 1/04* (2013.01); *C12R 1/01* (2013.01); *C12M 21/04* (2013.01); *C12M 25/20* (2013.01); *C12M 29/18* (2013.01)

(58) Field of Classification Search
None
See application file for complete search history.

(56) References Cited

U.S. PATENT DOCUMENTS 6,299,774 B1 * 10/2001 Ainsworth et al. ........... 210/603
2010/0304420 A1   12/2010 Gray

FOREIGN PATENT DOCUMENTS

WO   WO 2009034439 A2 *  3/2009

OTHER PUBLICATIONS

Lee, Kuo-Shing et al.; "Temperature effects on biohydrogen production in a granular sludge bed induced by activated carbon carriers". International Journal of Hydrogen Energy, 2005, pp. 1-8.
Lee, Kuo-Shing et al.; "Improving biohydrogen production in a carrier-induced granular sludge bed by altering physical configuration and agitation pattern of the bioreactor"; International Journal of Hydrogen Energy 31; 2006; pp. 1648-1657.
Levin, David B., et al.; "Biohydrogen production: prospects and limitations to practical application"; International Journal of Hydrogen Energy 29; 2004; pp. 173-185.
Valdez-Vazquez I, et al.; "Hydrogen production by fermentative consortia"; Renewable and Sustainable Energy Reviews 13; 2009; pp. 1000-1013.
Van Groenestijn, J.W., et al.; "Performance and population analysis of a non-sterile trickle bed reactor inoculated with Caldicellulosiruptor saccharolyticus, a thermophilic hydrogen produce"; Biotechnology and Bioengineering 102; 2009; pp. 1361-1367.
Wang Jianlong, et al.; "Factors influencing fermentative hydrogen production: A review"; Journal of Hydrogen Energy 34; 2009; pp. 799-881.
Zhang, Zhen-Peng, et al. Biohydrogen production with anaerobic fluidized bed reactors—A comparison of biofilm-based and granule-based systems; International Journal of Hydrogen Energy 33; 2008; pp. 1559-1564.
Zhang, Zhen-Peng, et al.; "Enhanced continuous biohydrogen production by immobilized anaerobic microflora"; Energy Fuels 22; 2008; pp. 87-92.
Zhang, Zhen-Peng, et al.; "Rapid formation of hydrogen-producing granules in an anaerobic continuous stirred tank reactor induced by acid incubation"; Biotechnology 96; 2007; pp. 1040-1050.
Zhang, Zhen-Peng, et al.; "Biohydrogen production in a granular activated carbon anaerobic fluidized bed reactor"; International Journal of Hydrogen Energy 32; 2007; pp. 185-191.
Valdez-Vazquez I, et al.; "Semi-continuous solid substrate anaerobic reactors for H2 production from organic waste: Mesophilic versus thermophilic regime"; International Journal of Hydrogen Energy 30; 2005; pp. 1383-1391.
Van Groenestijn, J.W., et al.; "Energy aspects of biological hydrogen production in high rates bioreactors operated in the thermophilic temperature range"; International Journal of Hydrogen Energy 27; 2002; pp. 1141-1147.
Das, Debabrata; "Advances in biohydrogen production processes: An approach towards commercialization"; International Journal of Hydrogen Energy (2009); pp. 1-9.
Davila-Vazquez, Gustavo, et al., "Fermentative hydrogen production in batch experiments using lactose, cheese whey and glucose: Influence of initial substrate concentration and pH"; International Journal of Hydrogen Energy 33 (2008); pp. 4989-4997.
Davila-Vazquez, Gustavo, et al., "Fermentative biohydrogen production: trends and perspectives"; Rev. Environ Sci Biotechnol (2008); pp. 27-45.
Hawkes, Freda R., et al., "Continuous dark fermentative hydrogen production by mesophilic microflora; Principles and progress"; International Journal of Hydrogen Energy 32 (2007); pp. 172-184.
Hallenbeck, Patrick C., et al.; "Advances in fermentative biohydrogen production: the way forward?"; Department of Microbiology and Immunology, University of Montreal (2009); pp. 287-297.

(Continued)

*Primary Examiner* — Renee Claytor
*Assistant Examiner* — Susan E Fernandez
(74) *Attorney, Agent, or Firm* — Osha • Liang LLP

(57) ABSTRACT

This invention relates to bioreactor processes, particularly bioreactor processes for the production of hydrogen gas from biomass, more particularly to bioreactor processes for the production of hydrogen gas employing a mixed anaerobic thermophilic bacterial consortium during the anaerobic fermentation of biomass.

11 Claims, 2 Drawing Sheets

(56) References Cited

OTHER PUBLICATIONS

Hallenbeck, Patrick C.; "Fermentative hydrogen production: Principles, progress, and prognosis"; International Journal of Hydrogen Energy (2009); pp. 1-11.

Rittmann, Bruce E.; "Opportunities for Renewable Bioenergy Using Microorganisms"; Biotechnology and Bioengineering, vol. 100, No. 2 (Jun. 2008); pp. 203-212.

Lee, Kuo-Shing, et al.; "Anaerobic Hydrogen Production With an Efficient Carrier-Induced Granular Sludge Bed Bioreactor"; Biotechnology and Bioengineering, vol. 87, No. 5 (Sep. 2004); pp. 648-657.

Hung, Chun-Hsiung, et al.; "Quantitative analysis of a high-rate hydrogen-producing microbial community in anaerobic agitated granular sludge bed bioreactors using glocose as substrate"; Appl Microbiol Biotechnol (2007); pp. 693-701.

Lee, Kuo-Shing, et al; "H2 production with anaerobic sludge using activated-carbon supported packed-bed bioreactors"; Biotechnology Letters (2003); pp. 133-138.

Tsygankov, A.A.; "Biological Generation of Hydrogen"; Russian Journal of General Chemistry (2007), vol. 77, No. 4; pp. 685-693.

Liu, Xuemei, et al.; "Recent advances in fermentative biohydrogen production"; Progress in Natural Science 18 (2008); pp. 253-258.

Lee, Hyung-Sool, et al.; "Evaluation of Metabolism Using Stoichiometry in Fermentative Biohydrogen"; Biotechnology and Bioengineering (2008); pp. 1-10.

Lee, Hyung-Sool, et al.; "An Electron-Flow Model Can Predict Complex Redox Reactions in Mixed-Culture Fermentative BioH2: Microbial Ecology Evidence": Biotechnology and Bioengineering, vol. 104, No. 4, (Nov. 2009); pp. 687-697.

Levin, David B., et al.; "Challenges for biohydrogen production via direct lignocellulose fermentation"; International Journal of Hydrogen Energy 34 (2009); pp. 7390-7403.

O-Thong, Sompong, et al.; "High-rate continuous hydrogen production by Thermoanaerobacterium thermosaccharolyticum PSU-2 immobilized on heat-pretreated methanogenic granules"; International Journal of Hydrogen Energy 33 (2008); pp. 6498-6508.

Zhang, Meng-Lin, et al.; "Rapid and accurate determination of VFAs and ethanol in the effluent of an anaerobic H2-producing bioreactor using near-infrared spectroscopy"; Water Research 43 (2009) pp. 1823-1830.

Zhang, Jian-jun, et al.; "Physical and Hydrodynamic Properties of Flocs Produced During Biological Hydrogen Production"; Biotechnology and Bioengineering, vol. 88, No. 7 (Dec. 2004); pp. 854-860.

Zhang, Zhen-Peng, et al.; "The role of acid incubation in rapid immobilization of hydrogen-producing culture in anaerobic upflow column reactors"; International Journal of Hydrogen Energy 33 (2008); pp. 5151-5160.

Zhang, Zhen-Peng, et al.; "Characteristics of Rapidly Formed Hydrogen-Producing Granules and Biofilms"; Biotechnology and Bioengineering (2008); pp. 1-11.

International Preliminary Report on Patentability and Written Opinion; Issued Nov. 15, 2011 in corresponding PCT Application No. PCT/IB2010/052143 (7 pages).

\* cited by examiner

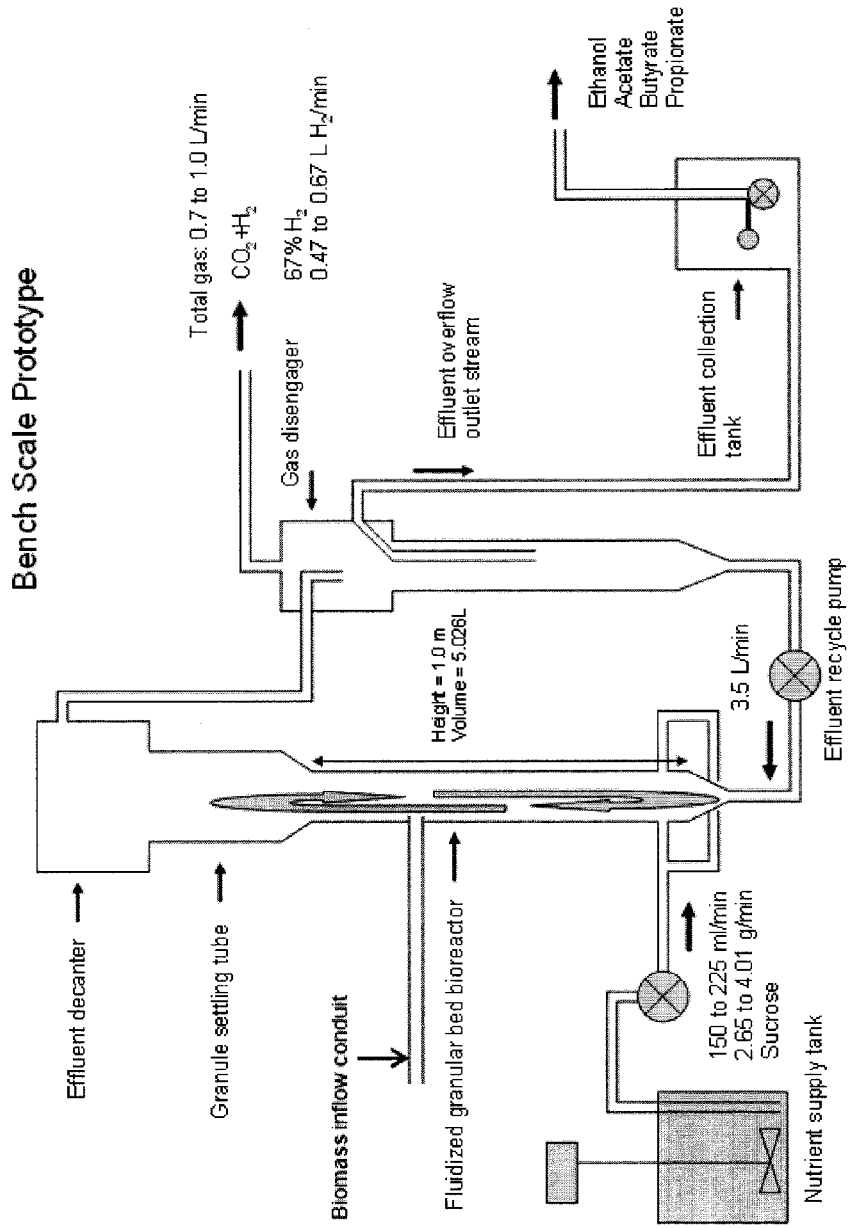
Figure 2. Scheme 1

BIOREACTOR PROCESS FOR PRODUCTION OF HYDROGEN FROM BIOMASS

FIELD OF THE INVENTION

This invention relates to bioreactor processes, particularly bioreactor processes for the production of hydrogen and/or carbon dioxide from biomass, more particularly to bioreactor processes for the production of hydrogen and/or carbon dioxide employing a mixed anaerobic bacterial consortium, particularly a mixed anaerobic thermophilic bacterial consortium, in the anaerobic fermentation of biomass or soluble hydrolysates derived from the hydrolysis of cellulosic materials including hemicellulose.

DEFINITIONS

The following terms contained in this patent specification are defined as follows:
"HP" hydrogen productivity
"HY" hydrogen yield

BACKGROUND OF THE INVENTION

The production of hydrogen and ethanol as well as other fermentation products from biomass, particularly plant biomass, is becoming an increasingly attractive option for alternative fuel production as prices of fossil fuels and petroleum increase. As fossil fuels become depleted alternative energy sources will become a crucial area of research both in industry and in academia.

In particular hydrogen is recognized as a clean and recyclable energy carrier and there is a prominent thrust in research initiatives focusing on the sufficient, efficient, profitable and "green" production of hydrogen gas. It is believed that hydrogen gas as an alternative energy carrier is indeed one of the more promising alternatives to be considered and exploited in the future. The use of biomass in the production of hydrogen gas provides for a "green" solution for hydrogen production which is hoped will be optimized and developed to provide a means for providing an economical and profitable supply of hydrogen gas. Furthermore, biological production of hydrogen from organic wastes as well as from other recyclable resources is considered preferable to the production of hydrogen from food crops for, while the hydrogen yield of food crops such as maize and wheat is relatively high, there is a global food shortage which is in danger of becoming exacerbated by the use of food crops in biological hydrogen producing reactors.

WO2009/034439, having the same inventor as the current application and fully incorporated hereto by reference, describes a bioreactor system for the rapid screening, selection and isolation of biofilm, floc and granule forming thermophilic bacteria or bacteria consortia that generate high levels of hydrogen from plant biomass including the soluble hydrolysates derived from the hydrolysis of cellulosic materials and particularly of cellulosic materials such as sugar cane waste and effluent that been subjected to only minimum pretreatment such as milling and wet heating.

Recent developments in utilizing fermentation processes in the production of hydrogen have pointed to advantages in using mesophiles and thermophiles in the process. Thermophiles, including extreme thermophiles, have many advantages as agents for the generation of biohydrogen from cellulose and from soluble hydrolysate derived from cellulose hydrolysis. Perhaps their main advantage is that high temperatures exclude microbial contamination from a bioreactor system. High temperatures also shift the equilibrium constant for the hydrogen generating reactions in the forward direction thereby increasing the hydrogen yield (HY). Most thermophiles and extreme thermophiles are, however, difficult to culture and maintain as pure cultures although it has been found that the hydrolysis of cellulosic materials and the generation of hydrogen from the products of this hydrolysis becomes increasingly favourable under the action of a mixed consortium of bacteria that includes anaerobic cellulolytic bacterial species.

The recent flood of reviews on biohydrogen production is an indication that current advances in biohydrogen generation technology has now entered or even gone beyond the mature phase of development (Das 2007; Davila-Vazquez et al 2007; Hallenbeck 2009; Hallenbeck and Gosh 2009; Hawkes et al 2007; Liu et al 2008; Tsyganov 2007; Valdez-Vazquez et al 2009). Attempts to improve both the productivity (HP) and yield (HY) of biohydrogen generation in dark anaerobic processes appears to have now also reached the point of diminishing returns (Rittmann 2008). Under most bioreactor design and operation conditions the maximum possible $H_2$ yield in the anaerobic oxidation of glucose to acetate has generally been observed not to exceed 4 mol $H_2$/mol glucose. In this reaction, of the 24 electron equivalents ($e^-$ eq) of glucose, 8 $e^-$ eq end up in $H_2$ and the remaining 16 $e^-$ eq end up in acetate. In dark fermentation the hydrogen yield (HY) appears to be "stuck" at 4 mol $H_2$/mol glucose (Rittmann 2008). Theoretically acetate could be further oxidized under anaerobic conditions to yield $4H_2$ and $2CO_2$ in the absence of methanogens if the partial pressure of $H_2$ in the bioreactor can be reduced. Whether or not a practically viable anaerobic single or multi-stage bioprocess could be engineered that would facilitate the complete oxidation of glucose to $12H_2$ remains an interesting, but controversial consideration (Hallenbeck 2009; Hallenbeck and Gosh 2009). It remains the general scientific consensus that formidable hurdles need to be overcome before the complete oxidation of glucose to hydrogen at high rates in a multiple stage process can be realized in practice (Hallenbeck and Gosh 2009).

The theoretical maximum value for hydrogen yield (HY) is 4 mol $H_2$/mol glucose. With respect to evaluating bioreactor performance, the critical threshold for the hydrogen yield (HY) can, for practical purposes, be set at 75% of the theoretical maximum, therefore 3 mol $H_2$/mol glucose.

It is of crucial importance to note that in practice hydrogen yield (HY) values equal to or exceeding 3 mol $H_2$/mol glucose are usually only attained in situations where the volumetric hydrogen productivity (HP) is several orders of magnitude below the critical limit of 120 mmol $H_2$/(L·h) (Levin et al 2004).

Conditions that favour high hydrogen yields (HY) can be summarized as follows: thermophilic temperatures, low substrate loading rates, low dilution rates (low hydraulic retention times), low hydrogen partial pressures and low bacterial biomass densities. In addition, $H_2$ gas stripping by sparging with $N_2$ is usually a necessary precondition for the achievement of hydrogen yields (HY) equal to or greater than 3 mol $H_2$/mol glucose. However under these conditions the hydrogen productivity (HP) is several orders of magnitude below the critical threshold of 120 mmol $H_2$/(L·h).

In all the instances where high hydrogen productivities (HP) have been achieved, the following bioreactor operational conditions have prevailed: high substrate loading rates, high dilution rates (high hydraulic rates of retention), and high bacterial biomass densities. Operational conditions that favour high hydrogen productivities (HP) also promote the maintenance of high hydrogen partial pressures within the bioreactor environment. High hydrogen partial pressures within the bioreactor environment do not favour the simultaneous attainment of hydrogen yields (HY) equal to or greater than 3 mol H2/mol glucose.

In general the conditions promoting high hydrogen productivities (HP) do not simultaneously favour the achievement of high hydrogen yields (HY). Recently published surveys show that less than 5% of all reported HY values from a wide diversity of experiments were equal to or greater than 3.0 mol $H_2$/mol glucose (Chong et al 2009; Das 2009; Davila-Vazquez et al 2007; Wang and Wan 2009).

Accordingly, there is a need for a bioreactor system that can utilize a mixed anaerobic bacterial consortium in order to concomitantly produce high HPs and high HYs.

OBJECT OF THE INVENTION

It is the object of this invention to provide for a bioreactor process for the production of high HPs and HYs, particularly for a bioreactor process providing for the substantially complete anaerobic conversion of biomass to hydrogen and carbon dioxide employing a mixed anaerobic thermophilic bacterial consortium.

SUMMARY OF THE INVENTION

According to a first aspect of the invention there is provided a bioreactor process for the substantial anaerobic conversion of biomass to at least hydrogen gas comprising:
 providing a reactor vessel having a bed consisting of a mixed anaerobic bacterial consortium;
 providing a biomass inflow into the reactor vessel via an inlet means, the rate of biomass inflow controlled by an inflow meter or an inflow variable pump, the biomass inflow at least partially fermented by the mixed anaerobic bacterial consortium of the reactor vessel to produce at least hydrogen gas;
 harvesting the at least hydrogen gas produced during fermentation inside the reactor vessel via a harvesting means;
 providing a degassed biomass effluent outflow exiting the reactor vessel via an outflow means, the treated biomass effluent outflow rate controlled by an outflow meter or an outflow variable pump; and
 recycling the degassed biomass effluent via a degassed effluent recycling means back into the reactor vessel, the rate of recycling controlled by a recycling flow meter or a recycling variable pump, wherein the ratio between the rate of recycling the degassed biomass effluent measured in litres per minute and the rate of replenishing the biomass inflow measured in litres per hour is smaller than or equal to one.

The bioreactor process wherein the ratio between the rate of recycling the degassed biomass effluent and the rate of replenishing the biomass inflow is less than or equal to 0.83.

The bioreactor process wherein the hydrogen yield is greater or equal to 4.0$H_2$/mol glucose and the hydrogen productivity is greater than 240 mmol $H_2$/(L·h).

The bioreactor process further comprising a reaction temperature of greater or equal to about 60° C.

The bioreactor process further comprising a hydraulic retention time of less than or equal to about 1 hour.

The bioreactor process wherein carbon dioxide gas is produced additionally to the hydrogen gas.

The bioreactor process wherein the mixed anaerobic bacterial consortium are immobilized as a biofilm on a carrier or as bacterial granule.

The bioreactor process wherein the mixed anaerobic bacterial consortium comprises at least thermophilic bacteria.

The bioreactor process wherein the biomass is plant biomass.

The bioreactor process wherein the biomass is animal biomass.

The bioreactor process wherein the biomass is a mixture of plant and animal biomass.

The bioreactor process wherein the biomass includes hexoses and volatile fatty acids.

The bioreactor process wherein the biomass is a soluble hydrosylate derived from hydrolysis of cellulosic material including hemicellulose.

The bioreactor process wherein the biomass is subjected to pretreatment being milling and/or wet heating before entering the reactor vessel.

The bioreactor process wherein the bed is a fluidized bed.

The bioreactor process wherein the bed is an expanded bed.

The bioreactor process wherein the bed consists of bacterial biofilm attached to a carrier or self-immobilized in the form of a bacterial granule.

The bioreactor process wherein the mixed anaerobic bacterial consortium in fed by at least one inorganic nutrient feed inlet.

The bioreactor process wherein a nutrient loading rate of the nutrient feed is greater or equal to 100 ml/min per reaction volume of about 5 litres and wherein the rate of recycling the degassed biomass effluent is greater than or equal to 2 L/min per reaction volume of about 5 litres.

The bioreactor process wherein a nutrient loading rate of the nutrient feed is greater or equal to 200 ml/min per reaction volume of about 2.53 litres and wherein the rate of recycling the degassed biomass effluent is greater than or equal to 3.5 L/min per reaction volume of about 2.53 litres.

According to a second aspect of the invention there is provided a method for screening, selecting and isolating biofilm or granule forming bacteria or bacteria consortia that generates high levels of hydrogen gas from biomass, said method comprising the following steps:
 (a) providing a reactor vessel having a bed suitable for colonization by a mixed consortium of bacteria;
 (b) introducing a mixed consortium of bacteria into the reactor vessel;
 (c) providing a biomass inflow into the reactor vessel via an inlet means, the rate of biomass inflow controlled by an inflow meter or an inflow variable pump, the biomass inflow at least partially fermented by the mixed anaerobic bacterial consortium of the reactor vessel to produce at least hydrogen gas;
 (d) providing for a degassed biomass effluent outflow exiting the reactor vessel via an outflow means, the treated biomass effluent outflow rate controlled by an outflow meter or an outflow variable pump; and
 (e) providing the reactor vessel with a degassed effluent recycling means recycling the degassed biomass effluent back into the reactor vessel, the rate of recycling controlled by a recycling flow meter or a recycling variable pump, wherein the ratio between the rate of recycling the degassed biomass effluent measured in litres per minute and the rate of replenishing the biomass inflow measured in litres per hour is smaller than or equal to one; and
 (f) isolating biofilm or granule forming bacteria or bacterial consortia from the bed.

The method for screening, selecting and isolating biofilm or granule forming bacteria or bacteria consortia, wherein the ratio between the rate of recycling the degassed biomass effluent and the rate of replenishing the biomass inflow is smaller than or equal to 0.83.

The method for screening, selecting and isolating biofilm or granule forming bacteria or bacteria consortia, further comprising a reaction temperature of greater or equal to about 60° C.

The method for screening, selecting and isolating biofilm or granule forming bacteria or bacteria consortia wherein the mixed anaerobic bacterial consortium are immobilized as a biofilm on a carrier or as bacterial granule.

The method for screening, selecting and isolating biofilm or granule forming bacteria or bacteria consortia, wherein the bacteria or bacteria consortia comprises at least thermophilic bacteria.

The method for screening, selecting and isolating biofilm or granule forming bacteria or bacteria consortia, wherein the biomass is plant biomass.

The method for screening, selecting and isolating biofilm or granule forming bacteria or bacteria consortia, wherein the biomass is animal biomass.

The method for screening, selecting and isolating biofilm or granule forming bacteria or bacteria consortia, wherein the biomass is a mixture of plant and animal biomass.

The method for screening, selecting and isolating biofilm or granule forming bacteria or bacteria consortia, wherein the biomass includes hexoses and volatile fatty acids.

The method for screening, selecting and isolating biofilm or granule forming bacteria or bacteria consortia wherein the biomass is a soluble hydrosylate derived from hydrolysis of cellulosic material including hemicellulose.

The method for screening, selecting and isolating biofilm or granule forming bacteria or bacteria consortia, wherein the biomass is subjected to pretreatment being milling and/or wet heating before entering the reactor vessel.

The method for screening, selecting and isolating biofilm or granule forming bacteria or bacteria consortia, wherein the bed is a fluidized bed.

The method for screening, selecting and isolating biofilm or granule forming bacteria or bacteria consortia, wherein the bed is an expanded bed.

The method for screening, selecting and isolating biofilm or granule forming bacteria or bacteria consortia, wherein the bed consists of bacterial biofilm attached to a carrier or self-immobilized in the form of a bacterial granule.

The method for screening, selecting and isolating biofilm or granule forming bacteria or bacteria consortia, wherein the mixed anaerobic bacterial consortium in fed by at least one inorganic nutrient feed inlet.

The method for screening, selecting and isolating biofilm or granule forming bacteria or bacteria consortia, wherein a nutrient loading rate of the nutrient feed is greater or equal to 100 ml/min per reaction volume of about 5 litres and wherein the rate of recycling the degassed biomass effluent is greater than or equal to 2 L/min per reaction volume of about 5 litres.

The method for screening, selecting and isolating biofilm or granule forming bacteria or bacteria consortia, wherein a nutrient loading rate of the nutrient feed is greater or equal to 200 ml/min per reaction volume of about 2.53 litres and wherein the rate of recycling the degassed biomass effluent is greater than or equal to 3.5 L/min per reaction volume of about 2.53 litres.

BRIEF DESCRIPTION OF THE DRAWINGS:

The following drawings are part of the present specification and are included to further demonstrate certain aspects of the invention. The invention may be better understood by reference to one or both of these drawings in combination with the detailed description presented herein.

FIG. 2 represents Scheme 1 showing a bioreactor system as designed and constructed and equipped and operated according to the bench scale bioreactor prototypes in OLS B 016 and OLS B 014.

DETAILED DESCRIPTION OF SPECIFIC EMBODIMENTS OF THE INVENTION

Figure 1:
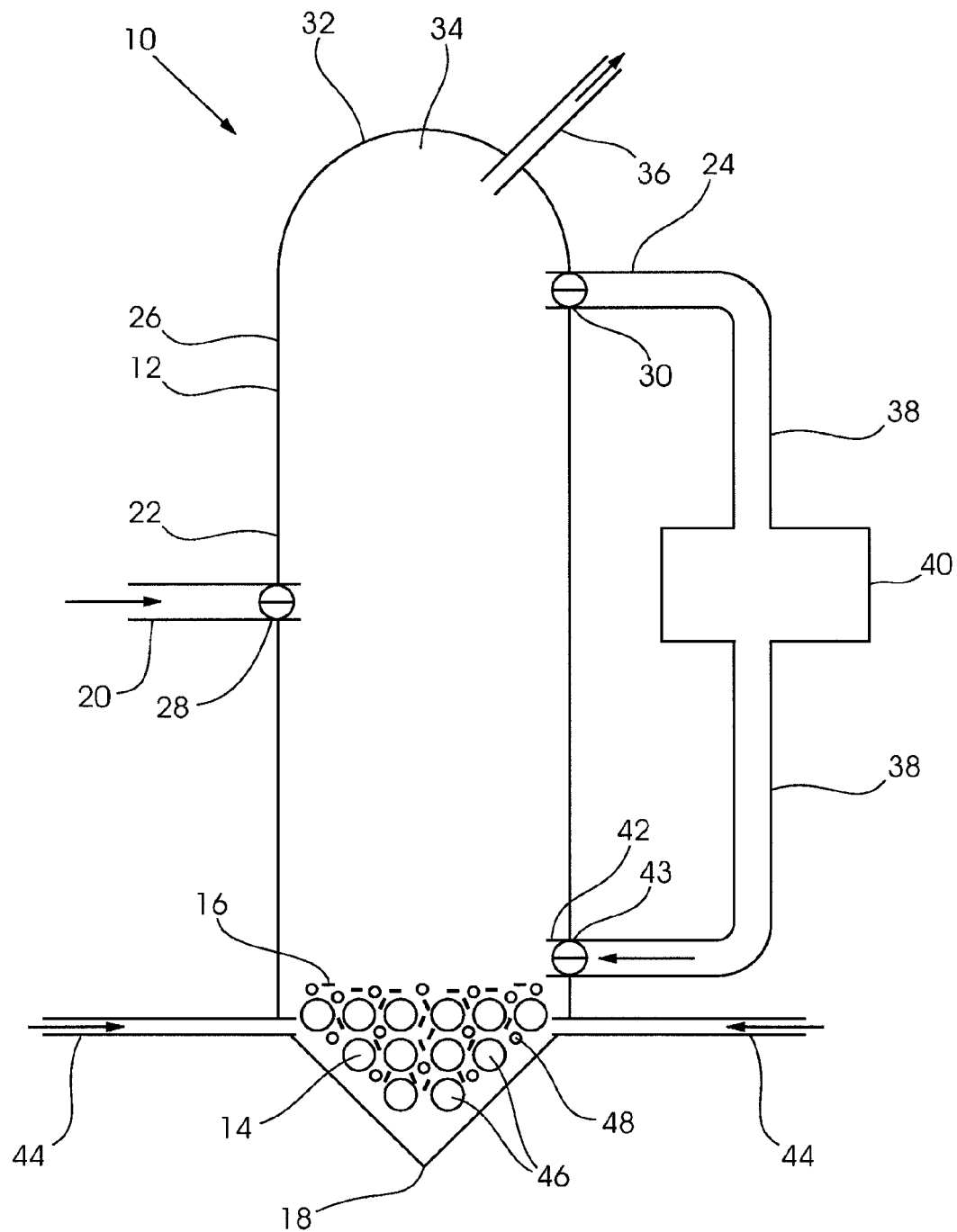
FIG. 1 is a bioreactor for producing hydrogen gas from biomass.

Referring to FIG. 1, a bioreactor 10 for producing hydrogen gas from biomass comprises a cylindrical reactor vessel 12 having a fluidized bed 14 of hydrogen producing bacteria 16 towards it base region 18. The reactor vessel 12 has a biomass inflow conduit 20 located substantially midway in the wall 22 of the reactor vessel 12, and a degassed biomass effluent outflow conduit 24 located substantially toward the upper end 26 of the reactor vessel 12.

The rate of biomass inflow into the reactor vessel 12 through the biomass inflow conduit 20 being controlled by an inflow meter 28. The rate of degassed biomass effluent outflow out of the reactor vessel 12 through the biomass effluent outflow conduit 24 being controlled by an outflow meter 30. The reactor vessel 12 has a conical top 32 which serves as a gas harvesting means 34. The harvested gas is led from the reactor vessel 12 by a gas discharge conduit 36. The treated degassed biomass effluent is recycled through a recycling conduit 38 by a recycling pump 40 into an inlet 42 near the base region 18 of the reactor vessel 12. The rate at which the recycled degassed biomass effluent is received back into the reactor vessel 12 is determined by the recycling flow meter 43.

The reactor vessel 12 also has a pair of inorganic nutrient feed conduits 44 which introduce inorganic nutrients into the base of the vessel 18 to promote and, where necessary, sustain the growth of bacteria in the reactor vessel 12.

The hydrogen producing bacteria is a mixed consortium of mesophylic and/or thermophilic bacteria that includes anaerobic cellulolytic bacteria. In use, the bacteria making up the mixed consortium are selected from one or more of a range of mesophylic and/or thermophilic habitats including primary sewage, soils, compost and rumen dung and they are adapted to temperatures ranging from 25° C. to 75° C.

The hydrogen producing bacterial consortium forms a biofilm in the bed which is formed by a particulate material bed 46 overlaid with activated carbon particles 48. The particulate material of the bed 46 is formed by one or more of steel balls, gravel, glass beads, coal ash particles and the like.

It is also envisaged that the treated plant biomass is an insoluble cellulosic plant material that has been subjected to only minimum pretreatment being milling and/or wet heating. Alternatively the treated plant biomass can be a soluble hydrolysate derived from hydrolysis of cellulosic material or it can be a mixture of insoluble cellulosic material and a hydrolysate derived from hydrolysis of cellulosic material.

PREPARATION AND USE EXAMPLES

Following the successful induction of bacterial granulation at 65° C. the HP and HY results were observed to be similar to those obtained by Lee et al (2006) for a mesophilic bioreactor. Hence the work of Lee et al (2006) and Zhang et al (2008) could be reproduced at the thermophilic level. However, in order to simultaneously increase HY it was discovered that the bioreactor system and operational conditions had be modified in significant ways which have not been done previously. Firstly, the total volume of the bioreactor system relative the effluent volume recycle flux was reduced substantially. The total system volumes of the original prototypes ranged from 10 L to 18 L. A settling column placed above the 5.0 L bioreactor contributed to the increases in the total system volume. The settling column was incorporated in the bioreactor design to function as a granule settling tank. Bioreactors with settling columns always had HY less than 2 mol $H_2$/mol glucose. Removal of the settling column had an effect on HY. Secondly, following the reduction in the volume of the bioreactor system, the effluent recycle rate for a bioreactor with a working volume of 2.53 L was maintained at 3.5 L $min^{-1}$ and the dilution rate was increased. All these modifications resulted in an increase in the HY (Table 1) confirming that high HYs and HPs could be simultaneously achieved. In addition, Table 2 shows that as temperature was increase at high influent flow rates and at high effluent recycle rates the following results where obtained:

TABLE 1

HP and HY values obtained at 65° C. for a bioreactor with a total system volume of 5.03 L which included 2.53 L for the bioreactor and 2.5 L for the gas-disengager and piping.

| HRT h | pH | Influent rate L/h | L $H_2$/ (L·h) HP | mmol $H_2$/ (L·h) HP | mol $H_2$/ mol gluc HY |
|---|---|---|---|---|---|
| 4.17 | 7.8  | 1.8 | 0.34 | 12.76  | 0.66 |
| 4.17 | 6.23 | 1.8 | 0.64 | 23.92  | 1.12 |
| 2.79 | 5.98 | 2.7 | 1.35 | 50.65  | 1.31 |
| 2.79 | 5.72 | 2.7 | 3.71 | 138.97 | 3.44 |
| 3.6  | 5.06 | 3.6 | 4.6  | 172.24 | 3.43 |
| 4.5  | 5.43 | 4.5 | 6.25 | 234.1  | 3.42 |
| 4.5  | 5.81 | 4.5 | 6.84 | 255.97 | 3.26 |

The effluent recycle rate was 3.5 L $min^{-1}$. The sucrose concentration in the effluent was 17.8 g $L^{-1}$.

TABLE 2

HP and HY values obtained for range of temperatures for a bioreactor with a total system volume of 5.03 L which included 2.53 L for the bioreactor and 2.5 L for the gas-disengager and piping.

| Temp ° C. | Influent rate L/h | % $H_2$ | Total $H_2$ production L $H_2$/h | Total $H_2$ production mol $H_2$/h | Total sucrose consumed mol $H_2$/h | HY sucrose mol$H_2$/mol sucrose | HY glucose mol$H_2$/mol glucose | pH | Acetate mM | Propionate mM | Butyrate mM |
|---|---|---|---|---|---|---|---|---|---|---|---|
| 45 | 4.5 | 40 | 10.56 | 0.362 | 0.06  | 4.426 | 2.213 | 5.5 | 24.2  | 29.99 | 20.89 |
| 50 | 4.5 | 40 | 12.0  | 0.411 | 0.097 | 4.624 | 2.124 | 5.5 | 15.81 | 12.01 | 4.71  |
| 55 | 4.5 | 41 | 13.53 | 0.464 | 0.1   | 4.624 | 2.314 | 5.7 | 13.86 | 11.74 | 3.25  |
| 60 | 4.5 | 55 | 18.15 | 0.622 | 0.104 | 5.997 | 2.998 | 6.0 | 7.04  | 0.96  | 0.16  |
| 65 | 4.5 | 60 | 18.0  | 0.617 | 0.107 | 5.755 | 2.878 | 7.2 | 4.72  | 0.43  | 0.05  |
| 70 | 4.5 | 62 | 18.6  | 0.618 | 0.08  | 8.016 | 4.008 | 7.8 | 4.33  | 0.32  | 0.02  |

The effluent recycle rate was 3.5 L $min^{-1}$. The sucrose concentration in the effluent was 17.8 g $L^{-1}$ (1) High HYs and HPs were simultaneously achieved.

(2) Volatile fatty acids (VFAs) such as acetate, butyrate and propionate decreased, indicating that at temperatures greater than 55° C. under these bioreactor operation conditions the oxidation of acetate, butyrate and propionate became thermodynamically favourable.

Carbon balance analysis in terms of COD analysis confirmed that VFAs oxidation was taking place at temperatures greater than 55° C. Under these operational conditions VFAs were being oxidized to hydrogen. This result is consistent with further experimental results that gave HYs greater than 4 mol $H_2$/mol glucose.

In addition, the operation of a bioreactor of the type mentioned above for the production of high rates of hydrogen from plant biomass hydrolysates allows for the rapid screening, selection and isolation of biofilm or granule forming anaerobic thermophilic bacteria or bacteria consortia which include anaerobic acetate, butyrate and propionate oxidizing syntrophic bacteria which acting together bring about the generation of high levels of hydrogen from plant biomass or from soluble hydrolysates derived from the hydrolysis of cellulosic materials including hemicellulose. The methodology for operating the bioreactor facilitates the anaerobic oxidation of both hexoses and volatile fatty acids, greatly increasing the overall efficiency of the fermentation process.

By using the bioreactor system as designed and constructed and equipped and operated according to the bench scale bioreactor prototypes in OLS B 016 and OLS B 014, as shown in FIG. 2 (Scheme 1), and applying Endo medium at high loading rates (210 ml/min), containing 17.8 g/L sucrose, and recycling the effluent at rates of 3500 ml/min the following biohydrogen outputs have been achieved:

1. % $H_2$ generated>60%.
2. Total bioreactor hydrogen output>59.0 L $H_2$/h
3. Specific volumetric hydrogen productivity>11 L $H_2$/(L·h) or >340 mmol L $H_2$/(L·h)

These results were achieved with sucrose loading rates of 224.28 g/h for a bioreactor prototype with a bioreaction volume of 5.025 L. More than 96% of the sucrose substrate was utilized. The main bioreactor output products were biohydrogen and acetate. A detail record of the data is attached in the accompanying Table 1.

The design, construction and operation of the prototype bioreactor which is a fluidized granular bed bioreactor, with inoculum derived from either sewage or manure, allows for the production of biohydrogen to achieve levels which makes the entire system commercially viable.

The inoculum is preconditioned and enriched with bacteria consortia by the following treatments:

Pre-Bioreactor Inoculation Enrichment Treatment

1. Inoculum can be derived from either sewage sludge or cow dung or a mixture of both.

2. Incubation at pH 2.0 at 65° C. for 12 to 24 hours.
3. Followed by incubation at 90 to 95° C. for 1 h.
4. pH adjusted to pH 7.5 with Endo medium.
5. Inoculum was maintained at 65° C. by sub-subculturing on Endo medium.

Post-Bioreactor Inoculation Enrichment Treatment
1. Incubation for 12-24 h at pH 2.0 and temperature at 70° C.
2. Incubation for 12-24 h in 3× concentrated Endo medium at 45° C.
3. Bacterial granulation is induced by recycling degassed effluent through the bioreactor at rates between 2.0 and 3.5 L/min and by increasing influent feed rates at 24 h intervals from an initial rate of 10 ml to rates up to 200 ml/min. Granules can be induced at any temperature between 45 or 65° C. However reliable granulation occurs at 65° C. Once granulation has been initiated temperatures can be increased up to 70° C.
4. As the bacterial granules becomes adapted to temperatures between 65 and 75° C., the tensile strength of the granules increase and they can withstand high shear forces without disintegrating.
5. The bioreactor following this bacteria enrichment protocol can be operated at any one of the following temperatures: 37, 40, 45, 50, 55, 60, 65 and 70° C.

Methodology for the Simultaneous Increasing of HY and HP
1. A fluidized granular bed offers a number of degrees of freedom with respect to process operation variables such as HRT and effluent recycling.
2. The fluidized or suspended granular bed can be conceptualized as a stationary system through which the mobile bulk fluid phase moves at a velocity equal to the granule settling velocity. This phenomenon facilitates maximum mass transfer of both nutrients and gas molecules ($H_2$ and $CO_2$) between the mobile bulk fluid phase and the fluidized granular phase.
3. The rate of $H_2$ removal from the granular bed is directly proportional to the volume flux of the fluid phase (mixture of degassed recycled effluent and nutrient influent) through the fluidized or expanded granular bed.
4. Recycling of degassed effluent at high volume fluxes together with nutrient influent at high dilution rates through fluidized granular been facilitates highly efficient stripping of hydrogen from the bioreactor bed.
5. At temperature between 55 and 70° C. with degassed effluent recycling rates great between 2.0 and 3.5 L/min and influent supply rates between 3.0 and 4.2 L/h for a 2.53 L bioreactor the % $H_2$ content increased from 40 to >60%, the HY increased from 2.0 to >3 mol $H_2$/mol glucose, HP from 100 to >240 mmol $H_2$/(L·h).
6. To achieve % $H_2$ content, HYs and HPs greater than 60%, HYs greater than 4.0$H_2$/mol glucose and HPs greater than 240 mmol $H_2$/(L·h), respectively, the ratio of the degassed effluent recycling rate to bioreactor volume should be less than 1.0.
7. Application of the following bioreactor operation parameters: HRT<1 h; effluent recycle rate to bioreactor volume smaller than 1.0 and an operational temperature greater that 60° C. promoted the almost complete oxidation of VFAs which in turn resulted in an increase in HY to values greater than the so-called theoretical maximum of 4 mol H2/mol glucose.
8. With the almost complete oxidation of acetate, butyrate and propionate, this bioreactor operational system brings about the almost complete conversion of hexose substrate into bacterial biomass, $H_2$ and $CO_2$.
9. When the settled granular bed is less than 25% of the bioreactor height then applications of HRTs less 1 h will result in a sucrose washout level approaching 50%. Thus sucrose conversion efficiency will be increased if the effluent overflow of the first bioreactor is passed through one or more bioreactors connected in series. Each bioreactor in the series will be connected to gas disengager with the ratio degassed effluent recycling rates to bioreactor volume not being less than 1.0. This will result in the complete conversion of hexoses to into bacterial biomass, $H_2$ and $CO_2$. The effluent output of last bioreactor will contain no VFAs, only bacterial biomass.
10. The bacterial biomass in the effluent of the final bioreactor can be used as the feed stock for the production of methane in an upflow anaerobic sludge bed bioreactor. This operational system allows for high rate conversion of hexose into $H_2CH_4$ and $CO_2$.

REFERENCES

Das D (2009) Advances in biohydrogen production processes: An approach to commercialization. International Journal of Hydrogen Energy Davila-Vazquez G, Arriaga S, Alatriste-Mondragon F, de Leon-Rodriquez A, Rosales-Colunga L, Razo-Flores E (2007) Fermentative biohydrogen production: trends and perspectives. Review of Environmental Science and Biotechnology Hallenbeck P C (2009) Fermentative hydrogen production: principles, progress, and prognosis. International Journal of Hydrogen Energy 34: 7379-7389.

Hallenbeck P C, Gosh D (2009) Advances in fermentative biohydrogen production: the way forward? Trends in biotechnology 27:

Hawkes F R, Hussy I, Kyazza G, Dinsdale R, Hawkes D L (2007) Continuous dark fermentative hydrogen production by mesophilic microflora: principles and progress. International Journal of Hydrogen Energy 32: 172-184.

Lee K S, Wu J F, Lo Y S, Lo Y C, Lin P J, Chang J S (2004) Anaerobic biohydrogen production with an efficient carrier-induced granular sludge bed bioreactor. Biotechnology and Bioengineering 87: 648-657.

Lee K S, Lin P J, Chang J S (2005) Temperature effects on biohydrogen production in a granular sludge bed induced by activated carbon carriers. International Journal of Hydrogen Energy Lee K S, Lo Y C, Lin P J, Chang J S (2006) Improving biohydrogen production in a carrier-induced granular sludge bed by altering physical configuration and agitation pattern of the bioreactor. International Journal of Hydrogen Energy 31: 1648-1657.

Lee K S, Wu J F, Lo Y C, Lin P J, Chang J S (2004). Anaerobic hydrogen production with an efficient carrier-induced granular sludge bed bioreactor. Biotechnology and Bioengineering 87: 648 0-657.

Lee K S, Lo Y C, Lin P J, Chang J S (2006) Improving biohydrogen production in a carrier-induced granular sludge bed by altering physical configuration and agitation pattern of the bioreactor. International Journal of Hydrogen Energy 31: 1648-1657.

Levin D B, Pitt L, Love M (2004) Biohydrogen production: prospects and limitations to practical application. International Journal of Hydrogen Energy 29: 173-185.

Liu X, Ren N, Song F, Yang C, Wang A (2008) Recent advances in fermentative biohydrogen production. Progress in natural science 18: 253-258.

O-Thong S, Prasertsan P, Karakashev D, Angelidaki I (2008) High-rate continuous hydrogen production by *Thermoanaerobacterium thermosaccharolyticum* PSU-2 immobilized on heat-pretreated methanogenic granules. International Journal of Hydrogen Energy 33: 6498-6508.

Rittmann B E (2008) Opportunities for renewable bioenergy using microorganisms. Biotechnology and Bioenergy 100: 203-212.

Stronach S M, Rudd T, Lester J N (1986). Anaerobic digestion processes in industrial wastewater treatment. Biotechnology Monographs. Springer-Verlag, Berlin.

Tsyganov A A (2007) Biological generation of hydrogen. Russian Journal of General Chemistry 77: 685-693.

Valdez-Vazquez I, Poggi-Varaldo H (2009). Hydrogen production by fermentative consortia. Renewable and Sustainable Energy Reviews 13: 1000-1013.

Van Groenestijn J W, Geelhoed J S, Goorissen H P, Meesters A J M, Stam A J M, Claassen P A M (2009) Performance and population analysis of a non-sterile trickle bed reactor inoculated with *Caldicellulosiruptor saccharolyticus*, a thermophilic hydrogen producer. Biotechnology and Bioengineering 102: 1361-1367.

Wang J, Wan W (2009) Factors influencing fermentative hydrogen production: A review. Journal of Hydrogen Energy 34: 799-881.

Zhang Z P, Adav S S, Show K T, Tay J H, Liang D T, Lee D J, Su A (2008 a). Characterization of rapidly formed hydrogen-producing granules and biofilm. Biotechnology and Bioengineering.

Zhang Z P, Show K Y, Tay J H, Liang D T, Lee D J (2008b) Biohydrogen production with anaerobic fluidized bed reactors—A comparison of biofilm-based and granule-based systems. International Journal of Hydrogen Energy 33: 1559-1564.

Zhang Z P, Show K Y, Tay J H, Liang D T, Lee D J (2008c) Enhanced continuous biohydrogen production by immobilized anaerobic microflora. Energy Fuels 22: 87-92.

Zhang Z P, Show K Y, Tay J H, Liang D T, Lee D J, Jiang W J (2007a) Rapid formation of hydrogen-producing granules in an anaerobic continuous stirred tank reactor induced by acid incubation. Biotechnology 96: 1040-1050.

Zhang Z P, Tay J H, Show K Y, Yan R, Liang D T, Lee D J, Jiang W J (2007b). Biohydrogen production in a granular activated carbon anaerobic fluidized bed reactor. International Journal of Hydrogen Energy 32: 185-191.

The invention claimed is:

1. A bioreactor process for the substantial anaerobic conversion of biomass to at least hydrogen gas comprising:
    providing a reactor vessel having a bed consisting of a mixed anaerobic bacterial consortium;
    providing a biomass inflow into the reactor vessel via an inlet means, wherein the biomass includes hexoses and volatile fatty acids, the rate of biomass inflow controlled by an inflow meter or an inflow variable pump, the biomass inflow at least partially fermented by the mixed anaerobic bacterial consortium of the reactor vessel to produce at least hydrogen gas;
    harvesting the at least hydrogen gas produced during fermentation inside the reactor vessel via a harvesting means;
    providing a degassed biomass effluent outflow exiting the reactor vessel via an outflow means, the treated biomass effluent outflow rate controlled by an outflow meter or an outflow variable pump; and
    recycling the degassed biomass effluent via a degassed effluent recycling means back into the reactor vessel, the rate of recycling controlled by a recycling flow meter or a recycling variable pump and at a temperature between 55° C. and 70° C. with degassed effluent recycling rates between 2.0 and 3.5 L/min and biomass inflow between 3.0 and 4.2 L/h for a reactor volume of 2.53 L;
    wherein the process has a hydrogen yield (HY) of at least 3 moles $H_2$ per mole of glucose and a specific volumetric hydrogen productivity of greater than 240 mmol $H_2/(L \cdot h)$.

2. The bioreactor process according to claim 1, further comprising a reaction temperature of greater or equal to about 60° C.

3. The bioreactor process according to claim 2, wherein the mixed anaerobic bacterial consortium are immobilized as bacterial granules, wherein the mixed anaerobic bacterial consortium comprises thermophilic bacteria and wherein the bed is either a fluidized bed or an expanded bed.

4. The bioreactor process according to claim 3, wherein the granules are manufactured according to a granule manufacturing process comprising:
    incubating inoculum derived from either sewage sludge or cow dung or a mixture of both at a pH of 2.0 and at a temperature of 65° C. for 12 to 24 hours;
    incubating the inoculum at a temperature from 90° C. to 95° C. for 1 h;
    adjusting the pH to a pH of 7.5 with Endo medium;
    maintaining the inoculum at a temperature of 65° C. by sub-subculturing on Endo medium;
    incubating the inoculum for 12-24 h at a pH of 2.0 and a temperature of 70° C.;
    incubating the inoculum for 12-24 h in a 3X concentrated Endo medium at a temperature of 45° C.;
    inducing bacterial granulation by recycling degassed effluent through the bioreactor at rates between 2.0 and 3.5 L/min and by increasing influent feed rates at 24 h intervals from an initial rate of 10 ml/min to rates up to 200 ml/min, for a reactor volume of 2.53 L;
    wherein granulation is induced at a temperature between 45° C. and 65° C. and once granulation has been initiated temperatures are increased up to 70° C.; and
    wherein as the bacterial granules become adapted to temperatures between 65° and 75° C., the tensile strength of the granules increase and they can withstand high shear forces without disintegration.

5. The bioreactor process according to claim 1, wherein the mixed anaerobic bacterial consortium are immoblized as a biofilm on a carrier, wherein the mixed anaerobic bacterial consortium comprises thermophilic bacteria and wherein the bed is either a fluidized bed or an expanded bed.

6. The bioreactor process according claim 1, wherein the mixed anaerobic bacterial consortium is fed by at least one inorganic nutrient feed inlet at a nutrient loading rate of greater or equal to 100 ml/min per reaction volume of 5 litres.

7. The bioreactor process according to claim 1, wherein the mixed anaerobic bacterial consortium is fed by at least one inorganic nutrient feed inlet at a nutrient loading rate of greater or equal to 200 ml/min per a reactor volume of about 2.53 litres and wherein the rate of recycling the degassed biomass effluent is equal to 3.5 L/min per a reactor volume of 2.53 litres.

8. The bioreactor process according to claim 1 having a hydraulic retention time of less than about 1 hour.

9. The bioreactor process according to any one of claims 1, 2, 5, 6, 3, 4, 7, and 8, wherein the biomass is subjected to pretreatment being milling and/or wet heating of the biomass before entering the reactor vessel.

10. The process of claim 1, wherein the at least hydrogen gas produced during fermentation inside the reactor vessel comprises greater than 60 mol % hydrogen.

11. The process of claim 1, wherein the process has a hydrogen yield (HY) of at least 4 moles $H_2$ per mole of glucose.

* * * * *